US005569241A

United States Patent [19]
Edwards

[11] Patent Number: 5,569,241
[45] Date of Patent: *Oct. 29, 1996

[54] THIN LAYER ABLATION APPARATUS

[75] Inventor: Stuart D. Edwards, Los Altos, Calif.

[73] Assignee: Vidacare, Inc., Menlo Park, Calif.

[ * ] Notice: The term of this patent shall not extend beyond the expiration date of Pat. No. 5,505,730.

[21] Appl. No.: 272,162

[22] Filed: Jul. 7, 1994

Related U.S. Application Data

[63] Continuation-in-part of Ser. No. 265,459, Jun. 24, 1994, Pat. No. 5,505,730.

[51] Int. Cl.$^6$ .................................................. A61B 17/39
[52] U.S. Cl. ........................ 606/41; 606/31; 606/39; 607/101; 607/102; 604/22
[58] Field of Search .................................... 606/7, 13–15, 606/27–34, 41, 42, 45–47, 191–193; 607/98–102; 604/53, 96–102, 21, 22

[56] References Cited

U.S. PATENT DOCUMENTS

| | | |
|---|---|---|
| 1,620,929 | 3/1927 | Wallerich . |
| 1,827,306 | 10/1931 | Chapman et al. . |
| 3,645,265 | 2/1972 | Majzlin . |
| 3,840,016 | 10/1974 | Lindemann . |
| 3,924,628 | 12/1975 | Droegemueller et al. . |
| 3,948,270 | 4/1976 | Hasson . |
| 4,057,063 | 11/1977 | Gieles et al. . |
| 4,676,258 | 6/1987 | Inokuchi et al. . |
| 4,799,479 | 1/1989 | Spears . |
| 4,865,047 | 9/1989 | Chou et al. . |
| 4,949,718 | 8/1990 | Neuwirth et al. . |
| 4,960,133 | 10/1990 | Hewson . |
| 4,961,435 | 10/1990 | Kitagawa et al. . |
| 4,979,948 | 12/1990 | Geddes et al. . |
| 5,084,044 | 1/1992 | Quint . |
| 5,186,181 | 2/1993 | Franconi et al. . |
| 5,188,122 | 2/1993 | Phipps et al. . |
| 5,191,883 | 3/1993 | Lennox et al. . |
| 5,232,444 | 8/1993 | Just et al. ................................. 604/96 |
| 5,263,493 | 11/1993 | Avitall ..................................... 607/122 |
| 5,277,201 | 1/1994 | Stern ........................................ 607/98 |
| 5,279,299 | 1/1994 | Imran ....................................... 128/642 |

OTHER PUBLICATIONS

Singer, et al.; *Preliminary Clinical Experience With A Thermal Balloon Endometrial Ablation Method To Treat Menorrhagia;* Obstetrics & Gynecology, vol. 83, No. 5, Part 1, May 1994; pp. 732–734.

Phipps, et al.; *Treatment Of Functional Menorrhagia By Radiofrequency–Induced Thermal Endometrial Ablation;* The Lancet, vol. 335; Feb. 17, 1990; pp. 374–376.

(List continued on next page.)

*Primary Examiner*—Angela D. Sykes
*Assistant Examiner*—Michael Peffley
*Attorney, Agent, or Firm*—Wilson Sonsini Goodrich & Rosati

[57] ABSTRACT

An ablation apparatus has a balloon that is inserted into an organ of a body and ablates all or a selected portion of the inner layer of the organ. Electrolytic solution fills the balloon, and the balloon includes a plurality of apertures from which electrolytic solution flows from the balloon. The flow rate of electrolytic solution is dependent on the pressure applied to the balloon by the electrolytic solution. A conforming member, with a conductive surface and a back side, is made of a material that substantially conforms to a shape of the inner layer of the organ and delivers the electrolytic solution and RF energy through the conductive surface to the inner layer. Advantageously, difficult to access areas are reached with the inclusion of the conforming member. Optionally positioned between the conforming member and the balloon is a porous membrane. A printed circuit can be formed in or on the conforming member, or adjacent to its back side or conductive surface, and delivers RF energy to selected sections of the inner layer. A feedback device is included and is responsive to a detected characteristic of the inner layer. The feedback device provides a controlled delivery of RF energy to segments of the circuit.

22 Claims, 16 Drawing Sheets

OTHER PUBLICATIONS

Phipps, et al.; *Experimental And Clinical Studies With Radiofrequency–Induced Thermal Endometrial Ablation For Functional Menorrhagia;* Obstetrics & Gynecology, vol. 76, No. 5, Part 1, Nov. 1990; pp. 876–881.

Prior, et al.; *Treatment Of Menorrhagia By Radiofrequency Heating;* Int. J. Hyperthermia, 1991, vol. 7, No. 2, pp. 213–221.

Mumford, et al.; *Sterilization Needs In The 1990'S: The Case For Quinacrine Nonsurgical Female Sterilization;* American Journal of Obstetrics & Gynecology, vol. 167, No. 5, Nov. 1992; pp. 1203–1207.

Neuwirth, et al.; *The Endometrial Ablator: A New Instrument;* Obstetrics & Gynecology, vol. 83, No. 5, Part 1, May 1994; pp. 792–796.

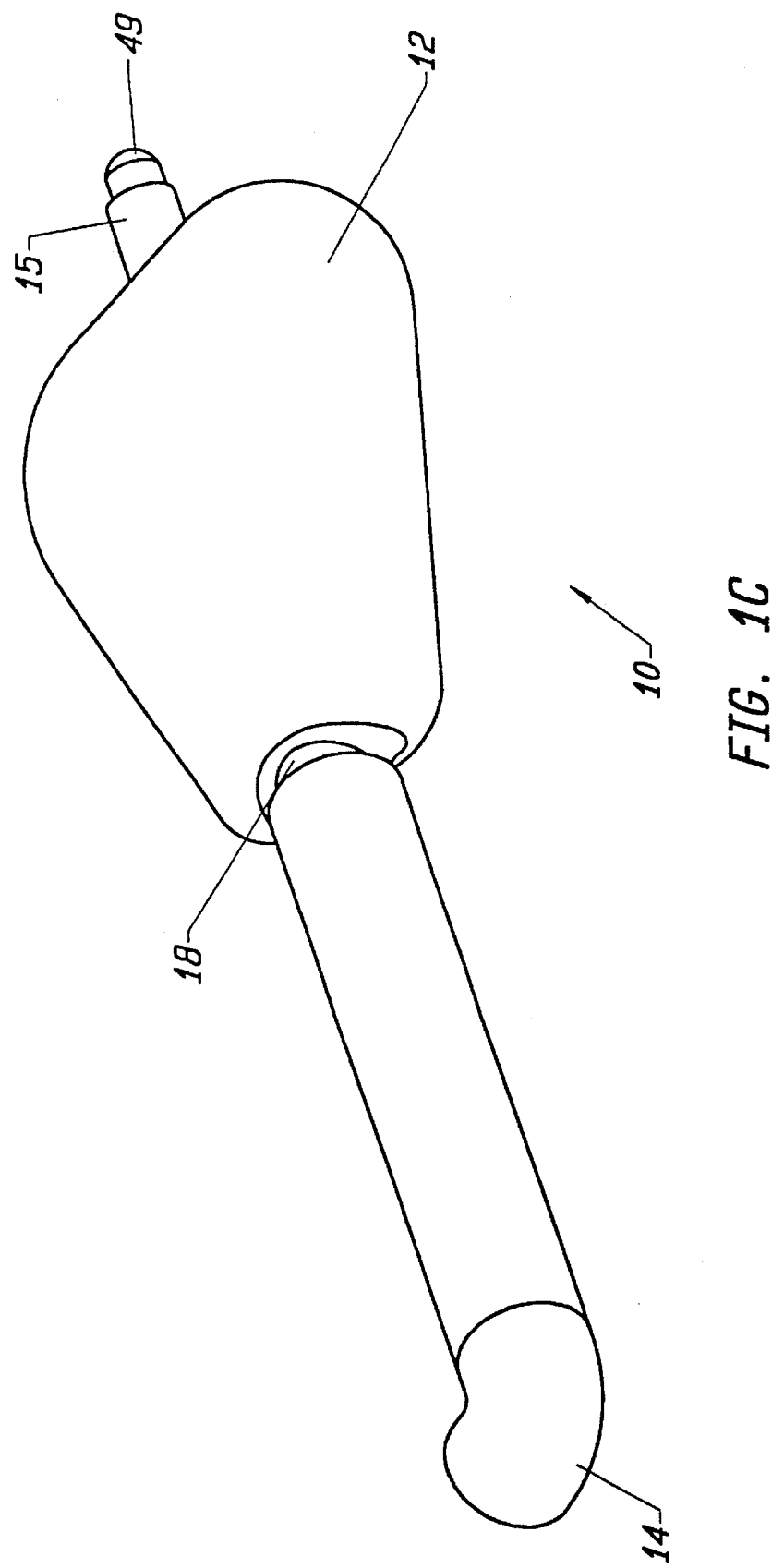

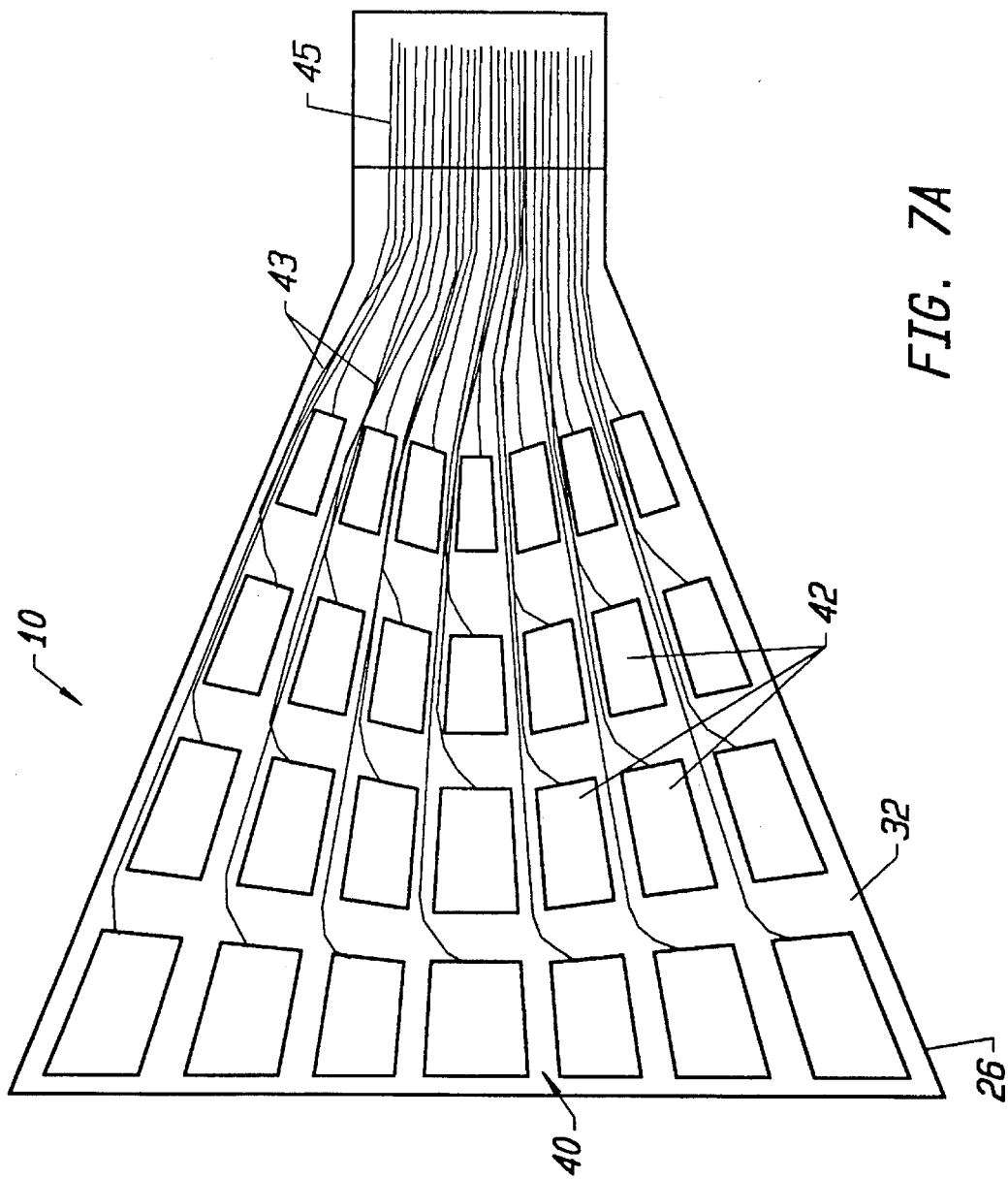

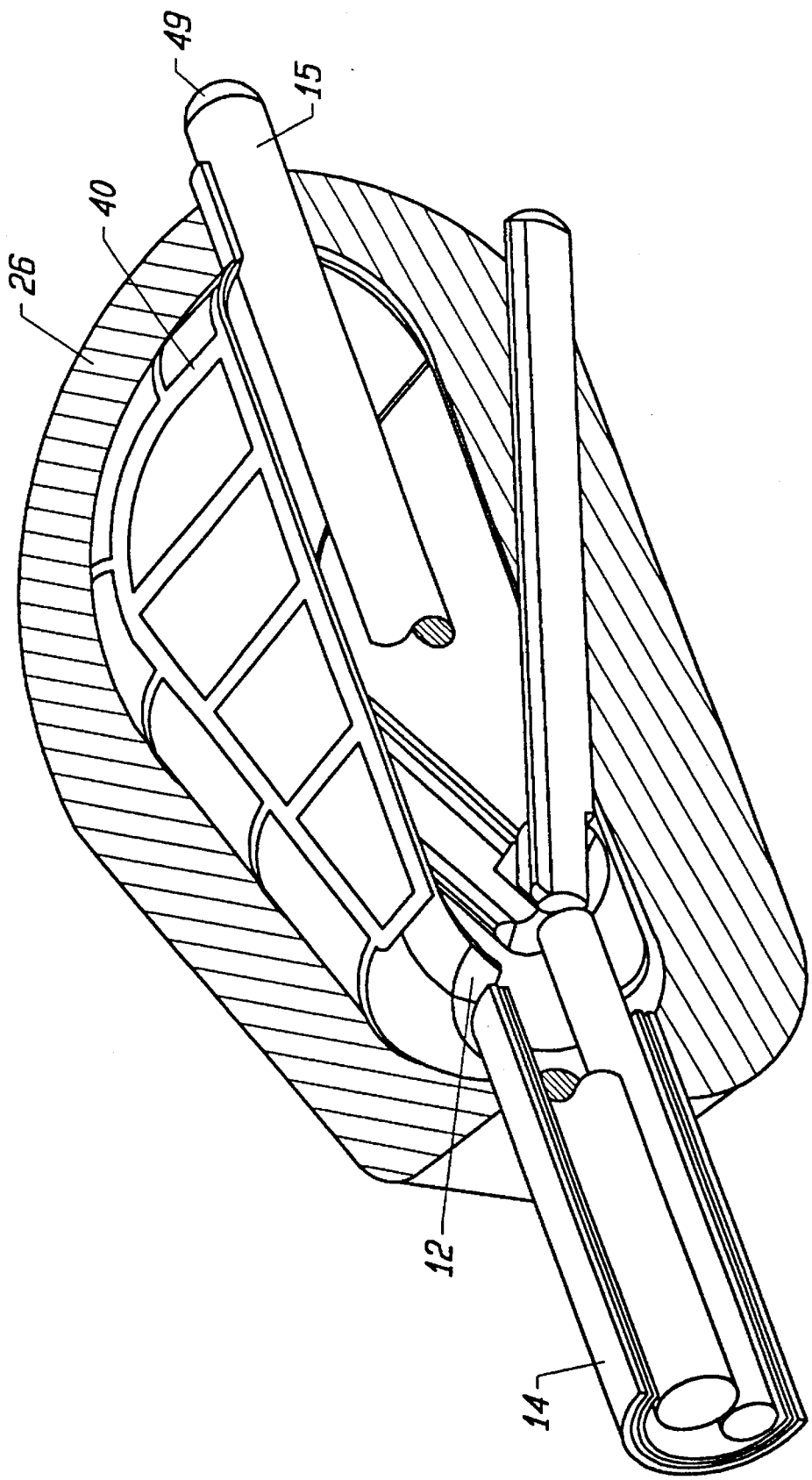

THIN LAYER ABLATION APPARATUS

CROSS-REFERENCE TO RELATED APPARATUS

This application is a continuation-in-part of U.S. patent Application Ser. No. 08/265,459 entitled "Thin Layer Ablation Apparatus" by Stuart Edwards, filed Jun. 24, 1994 now U.S. Pat No. 5,505,73, which is hereby incorporated by reference.

BACKGROUND OF THE INVENTION

1. Field of the Invention

This invention relates generally to an ablation apparatus for the selective ablation of the inner layers of body organs, and more particularly, to the endometrium layer of the uterus.

2. Description of Related Art

There are a number of body organs, including but not limited to the uterus, gall bladder, large intestine and the like, that have inner layers which have abnormal conditions. Traditional methods of treatment have included removal of the body organ to treat the abnormal condition, the use of lasers, and the application of a thermal source.

A diseased condition of the uterus, menorrhagia, is defined as excessive menstrual bleeding in the absence of organic pathology. It has no known aetiology and it has been postulated that it is due to an inappropriate exposure of the endometrium to hormones. Menorrhagia is an exceedingly common problem, typically comprising approximately one in five outpatient referrals to gynecological departments. Women suffering severe menorrhagia are at risk from chronic anemia. The first treatment employed may be the administration of drug therapy. A major disadvantage is the need to administer drugs long term, and frequently the beneficial effects are only temporary. Another treatment is hysterectomy.

A number of physical and chemical methods have been tried as alternatives to hysterectomy, including the use of superheated steam, cryotherapy, urea injection and radium packing. The most commonly used methods as an alternative to hysterectomy are, ablation of the endometrium either by using a laser, such as a Nd:YAG laser, or the use of RF energy applied with an electrode.

Laser treatments have provided only limited success. RF is an attractive alternative. In RF heating, a conductive probe is placed within the uterine cavity and an insulated ground-plane electrode or belt is placed around the patient's midriff. RF energy is applied to the thermal probe with the external belt electrode acting as the return arm of the circuit. The electrical load presented by the RF thermal probe, patient, and external belt is matched to the output of the RF generator via a tuning unit, to form a series resonant circuit. Once tuned, the majority of the power applied to the probe is deposited into the endometrium as heat.

Current flows primarily capacitively, and an electric field is set up around the active tip of the probe. Tissue lying within the field becomes heated because of rapid oscillation of charged particles and locally induced currents.

Prior et al have reported on the use of RF to treat menorrhagia. Power at 27·12 MHz was delivered to a probe that was placed into the uterine cavity and capacitively coupled to a second electrode consisting of a belt placed around the patient, Prior et al., Int. J. Hyperthermia, 1991, Vol. 7, No. 2, pgs 213 to 220. The active electrode was a 10 mm diameter stainless-steel cylinder with a length of 70 mm. This method, however, did not adequately deliver RF energy to the entire endometrium. Because the endometrium has an irregular surface, it is difficult to deliver sufficient RF energy to the entire structure and effective treat menorrhagia.

However, it is preferable if there is direct contact in order to treat the entire endometrium surface. In U.S. Pat. No. 5,277,201 (the "'201 patent") an electroconductive, expandable balloon expands the interior of the uterus and effects electrical contact with the endometrial lining to be destroyed. The device of the '201 patent fails, however, to provide sufficient physical contact with the entire endometrium, and thus the treatment is not complete. Not only is the physical contact with the endometrium unsatisfactory, but the effective delivery of RF energy to the endometrium could be improved.

There is a need for an RF ablation apparatus that provides more suitable conformation with a lining of a body organ, such as the endometrium of the uterus. Additionally, there is a need for an ablation device for the endometrium which includes a feedback mechanism that is responsive to detected characteristics of the endometrium, and the delivered RF energy is adjusted in response to the feedback.

SUMMARY OF THE INVENTION

An object of the invention is to provide an ablation apparatus suitable for interior thin walled areas of body organs.

Another object of the invention is to provide an ablation apparatus that effectively conforms to the shape of the interior of a body organ.

Yet another object of the invention is to provide an ablation apparatus that includes a printed circuit.

Still a further object of the invention is to provide an ablation apparatus that includes a feedback device in response to a detected characteristic of the endometrium, and the feedback provides a controlled delivery of RF energy to the endometrium.

Another object of the invention is to provide an ablation apparatus that includes a feedback device in response to a detected characteristic of the endometrium, as well as one or more ultrasound transducers.

Still a further object of the invention is to provide an ablation apparatus that includes a feedback device that monitors impedance and temperature at the endometrium.

Another object of the invention is to provide an ablation apparatus that includes a feedback device for the controlled delivery of RF energy to the endometrium and the impedance or a temperature profile of the endometrium is monitored.

A further object of the invention is to provide an ablation apparatus with a feedback device for the controlled delivery of RF energy, and the apparatus includes a conforming member made of an open foam type substance.

Still a further object of the invention is to provide an ablation apparatus with a feedback for the controlled delivery of RF energy, and the apparatus includes a microporous membrane.

These and other objects are achieved with an ablation apparatus for ablating an inner layer of an organ in the body. An inflatable member, such as a balloon, has an interior which houses an electrolytic solution. The balloon includes a plurality of apertures from which electrolytic solution is permitted to selectively flow from the interior, through one of apertures, at a flow rate that is dependent on the pressure applied to the balloon by the electrolytic solution. A conforming member, with a conductive surface, is made of a material that substantially conforms to a shape of the inner layer of the organ. Electrolytic solution and RF energy are delivered through the conductive surface to the inner layer. A circuit with segments is positioned in or on the conforming member and delivers RF energy to selected sections of the inner layer. The circuit can be formed on a member that is positioned adjacent to an interior side of the conforming member or adjacent to its conductive surface. A feedback device is included and is responsive to a detected characteristic of the inner layer. The feedback device provides a controlled delivery of RF energy to segments of the circuit.

A membrane can be included and positioned between the balloon and the conforming member. The membrane includes a plurality of apertures for receiving electrolytic solution from the balloon and delivering it to the conforming member and the inner layer of the organ.

The flow rate of electrolytic solution leaving the balloon, including but not limited to saline solution, is adjustable and depends on the pressure applied by the electrolytic solution to the balloon, typically caused by increasing or decreasing the amount of electrolytic solution in the balloon. The membrane is microporous, and the conforming member, which typically is a layer of a foam type material, both provide a controlled flow of electrolytic solution to the inner wall of the body organ. Additionally, the foam material of the conforming member is particularly pliable and suitable for conforming to the inner wall, and achieves an effective ablation of all or a part of the inner wall even when it has a very irregular surface.

The feedback device detects impedance or a temperature profile of the inner layer at a segment of the circuit. The amount of delivered RF energy is adjusted according to the detected impedance or temperature profile. Additionally included in the conforming member is one or more ultrasound transducers.

The conforming member provides a conductive surface that conforms to surfaces that have irregular shapes and with the feedback device, a controlled delivery of RF energy is delivered to the endometrium. The combinations of a printed circuit, conforming member and electrolytic solution provide for delivery of RF energy. Thus, RF energy can be effectively delivered to irregular surfaces. The feedback device provides controlled delivery of RF energy based on detected characteristics of the endometrium. The ablation apparatus is multiplexed between different segments.

The ablation apparatus of the invention is suitable for ablating a variety of surfaces of body organs including but not limited to the endometrium of the uterus.

DESCRIPTION OF THE DRAWINGS

FIG. 1(c) is a perspective view of an ablation device of the invention in a deployed position.

FIG. 7(a) is a perspective view of the invention with an inflatable device and a printed circuit that is segmented.

FIG. 7(c) is a cross-sectional, perspective view of the ablation apparatus of the invention, with the printed circuit positioned adjacent to an interior side of the conforming member.

DETAILED DESCRIPTION OF THE PREFERRED EMBODIMENTS

Figure 1A:
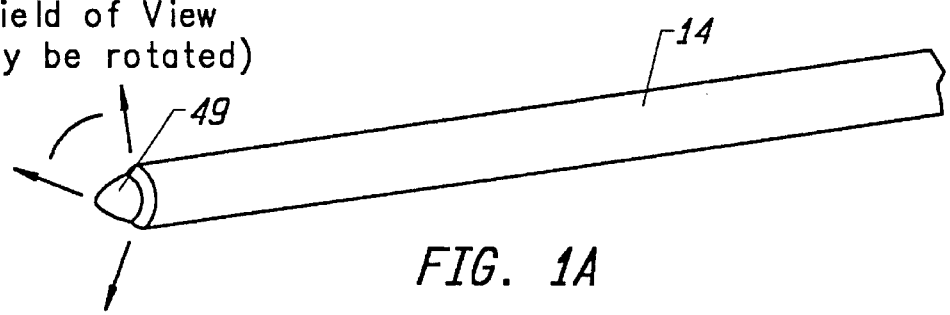
FIG. 1(a) is a perspective view of an ablation apparatus of the invention housed in an introducer sleeve and includes viewing optics.
Figure 1B:
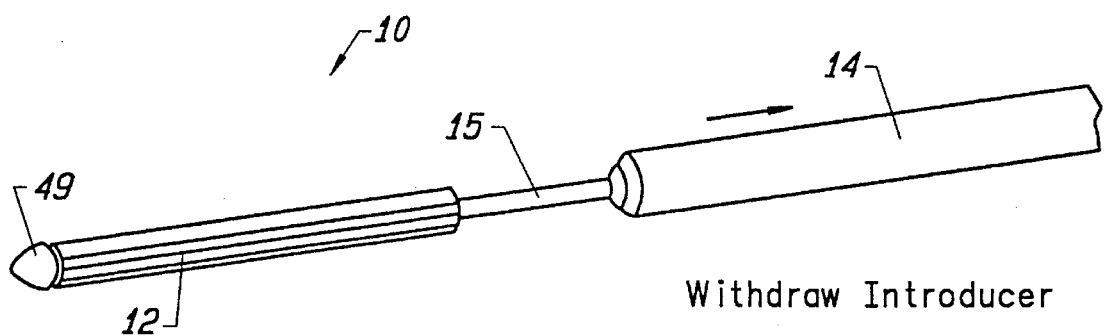
FIG. 1(b) is a perspective view of an ablation device of the invention in a non-deployed position as the introducer sleeve is withdrawn.
Figure 2:
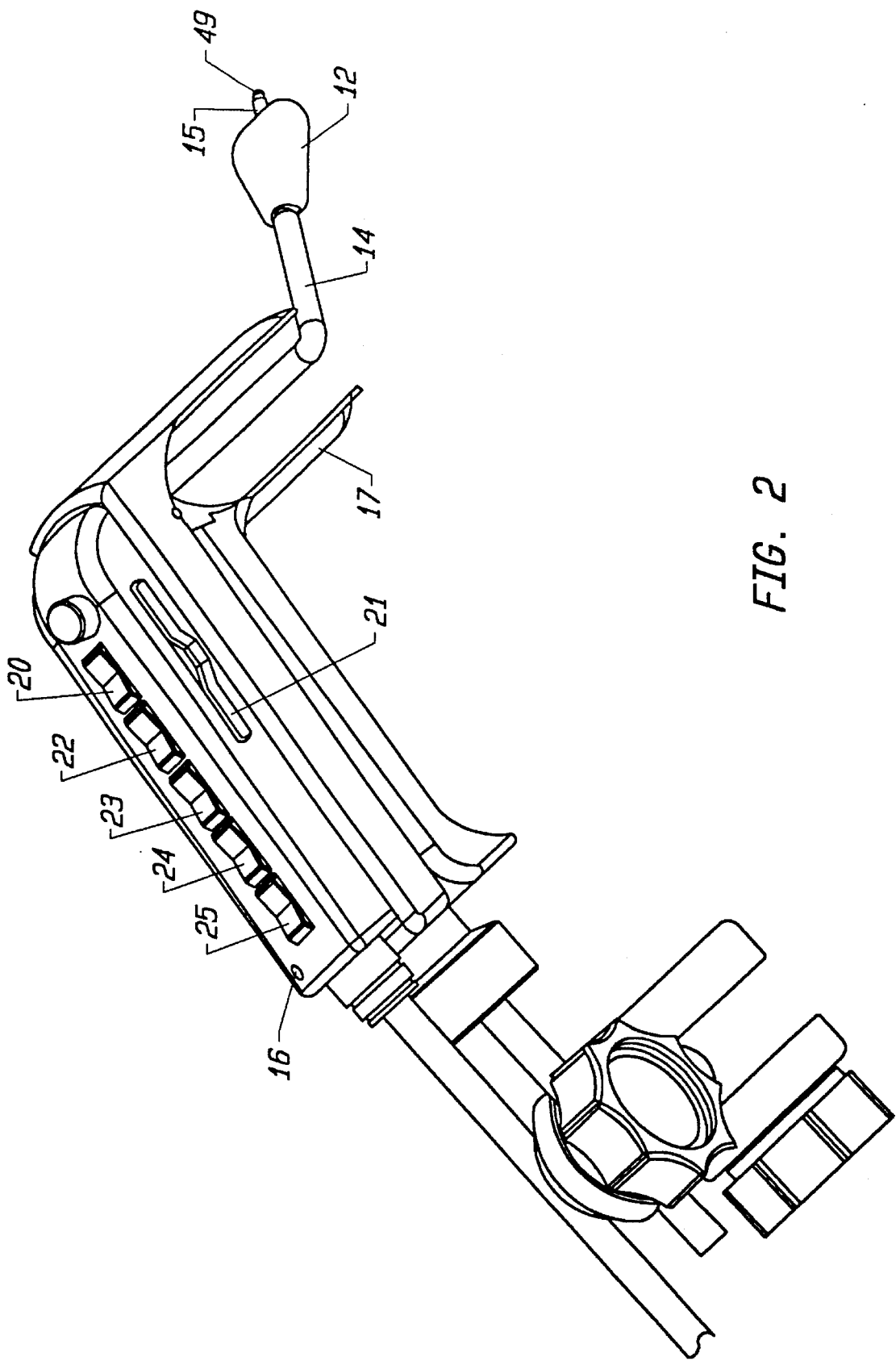
FIG. 2 is a perspective view of a handle associated with the ablation device of the invention. Included is a speculum and a clamp for mounting the ablation device.

An ablation apparatus 10 of the invention is illustrated in FIGS. 1(a), 1(b) and 1(c) and includes an inflatable member 12, including but not limited to a balloon, that is introduced into a desired body organ through an introducer sleeve 14 which can be attached to a handpiece 16 (FIG. 2). Balloon 12 is rolled or folded around a core lumen 15 which contains optics, fluid paths, sensor and electronic cabling and can be attached to a ratchet hinge 18 which imparts movement of balloon 12 when it is in a body organ. Ablation apparatus 10 can be generally rolled or folded around a core lumen 15 in order to provide a wringing type of motion. This can occur with the folding being accomplished in a helical manner. Balloon 12 is introduced through introducer sleeve 14 in a folded, or non-distended configuration. Introducer sleeve 14 can be of different cross-sectional sizes. In one embodiment it is small enough to be introduced into the cervix under local anaesthesia and can be on the order of about 3 mm in diameter.

Formed spring wires can be included in balloon 12 to assist in opening it to the deployed position. Positioned on handle 16 are a variety of actuators 20 through 25 which provide physician control of ablation apparatus 10, as more fully described hereafter. The actuators can be rocker switches, slider switches and the like. Ablation apparatus 10 is sufficiently opaque that it is visible under ultrasound.

A speculum 17 can attach to handle 16. Speculum 17 is used to distend the vagina, when ablation apparatus is used to ablate the endometrium of the uterus, in order to assist its introduction into the cervix. Once ablation apparatus 10 is inserted and deployed, speculum 17 is attached to handle 16. The treatment procedure can then proceed with a minimal amount of physician time spent on the actual treatment procedure.

Introducer sleeve 14 is introduced into the desired organ, as shown in FIG. 1(a), with balloon 12 in a non-deployed configuration. Following introduction, introducer sleeve 14 is withdrawn and can be retracted into handle 16. Introducer sleeve 14 can be of conventional design, such as an introducing catheter, well known to those skilled in the art. Balloon 12 can be swept from side to side, which movement is imparted by hinge 18. Hinge 18 also provides for the easy introduction of ablation apparatus 10 through the vagina, and into the cervix and uterus.

Generally, ablation apparatus 10 can be a mono-polar or bi-polar electrode system. It is capable of expanding so that balloon 12 becomes inflated within a selected body organ, and RF energy is delivered to an inner lining of the organ. RF energy is passed through the inner lining or surface for a time period selected that is sufficient to achieve the desired degree of ablation. This varies depending on the body organ. RF current flows through body tissue from a return electrode in the form of a conductive pad applied to the patient's outer skin. Maximum heating occurs where the current density is the greatest.

In one embodiment of the invention, the body organ is the uterus, and the lining is the endometrium. It will be appreciated that the present invention is not limited to the endometrium of the uterus and that other organs, including but not limited to the stomach, can also be treated with the invention.

Electric current flowing through the endometrium causes heating due to resistance of the tissue. Endometrial ablation can be accomplished as a relatively simple medical procedure with local anesthesia.

Figure 3:
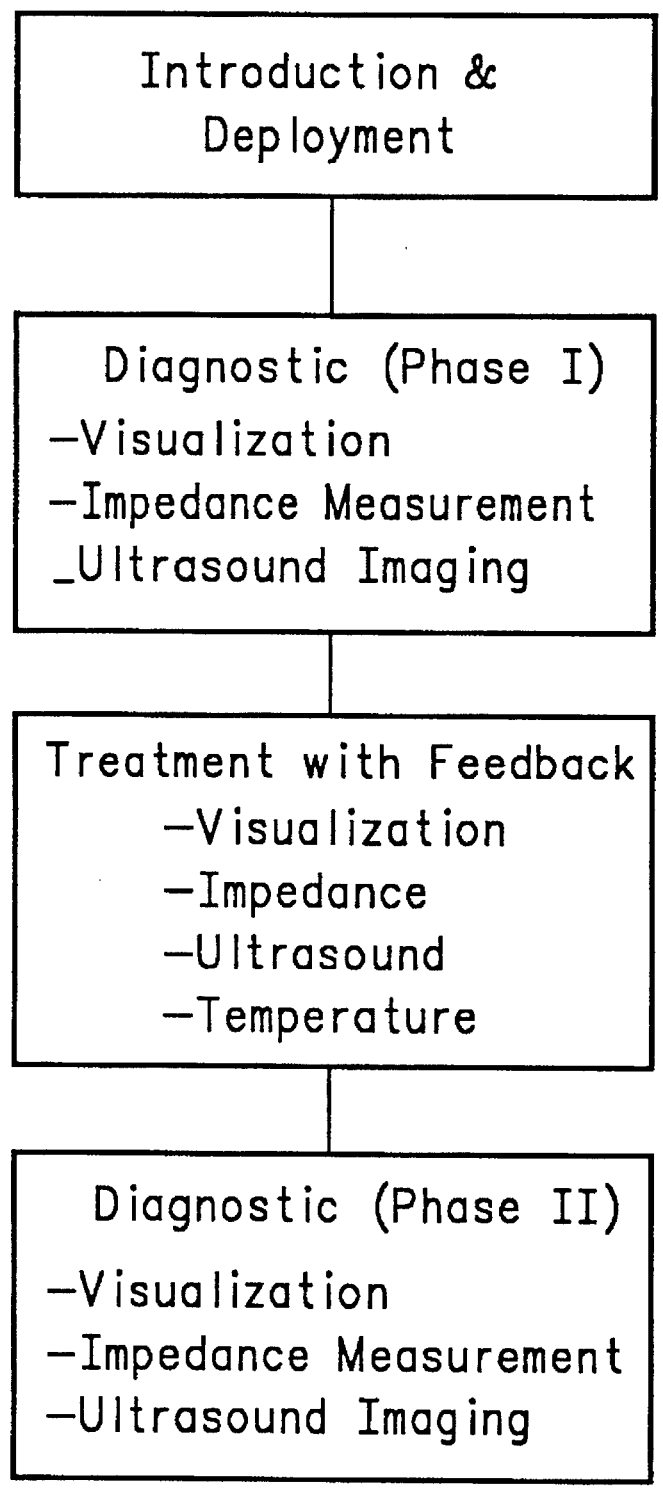
FIG. 3 is a flow chart listing the operation of the ablation device of the invention.

FIG. 3 is a flow chart illustrating the operation of ablation apparatus 10. Ablation apparatus 10 is first introduced into the uterus under local anaesthesia. Introducer sleeve 14 is then withdrawn and balloon 12 is expanded with the formed spring wires. Electrolytic solution is introduced into balloon 12, causing it to become distended and be self-retained in the uterus.

The diagnostic phase then begins. This is achieved through a variety of mechanisms, including but not limited to, (i) visualization, (ii) measuring impedance to determine the electrical conductivity between the endometrium and ablation device 10, and (iii) the use of ultrasound imaging to establish a base line for the tissue to be treated.

In the treatment phase, the ablation of the uterus is conducted under feedback control. This enables ablation device 10 to be positioned and retained in the uterus. Treatment can occur with minimal attention by the physician. Ablation apparatus 10 automatically conforms to the interior of the uterus, provides a relatively even flow of electrolytic solution to assist in the ablation, and a plurality of discrete circuits, either in the form of individual segments of a printed circuit, or a plurality of electrodes, are multiplexed in order to treat the entire endometrium and a portion of the myometrium. Feedback is accomplished by, (i) visualization, (ii) impedance, (iii) ultra-sound or (iv) temperature measurement. The feedback mechanism permits the turning on and off of different segments of the circuit in a desired ablative pattern, which can be sequential from one adjacent segment to the next, or it can jump around different segments. The amount of ablation can vary. However, it is desirable to ablate about 2 to 3 mm, with approximately 1 mm of the myometrium. Ultrasound can be used to create a map of the interior of the uterus. This information is input to a controller. Individual segments of the circuit are multiplexed and volummetrically controlled. The area of ablation is substantially the same for each ablation event. Even though there are folds and crevices in the endometrium, the entire endometrium is treated and evenly ablated.

A second diagnostic phase may be included after the treatment is completed. This provides an indication of ablation treatment success, and whether or not a second phase of treatment, to all or only a portion of the uterus, now or at some later time, should be conducted. The second diagnostic phase is accomplished through, (i) visualization, (ii) measuring impedance, (iii) ultrasound or (iv) temperature measurement.

Figure 4:
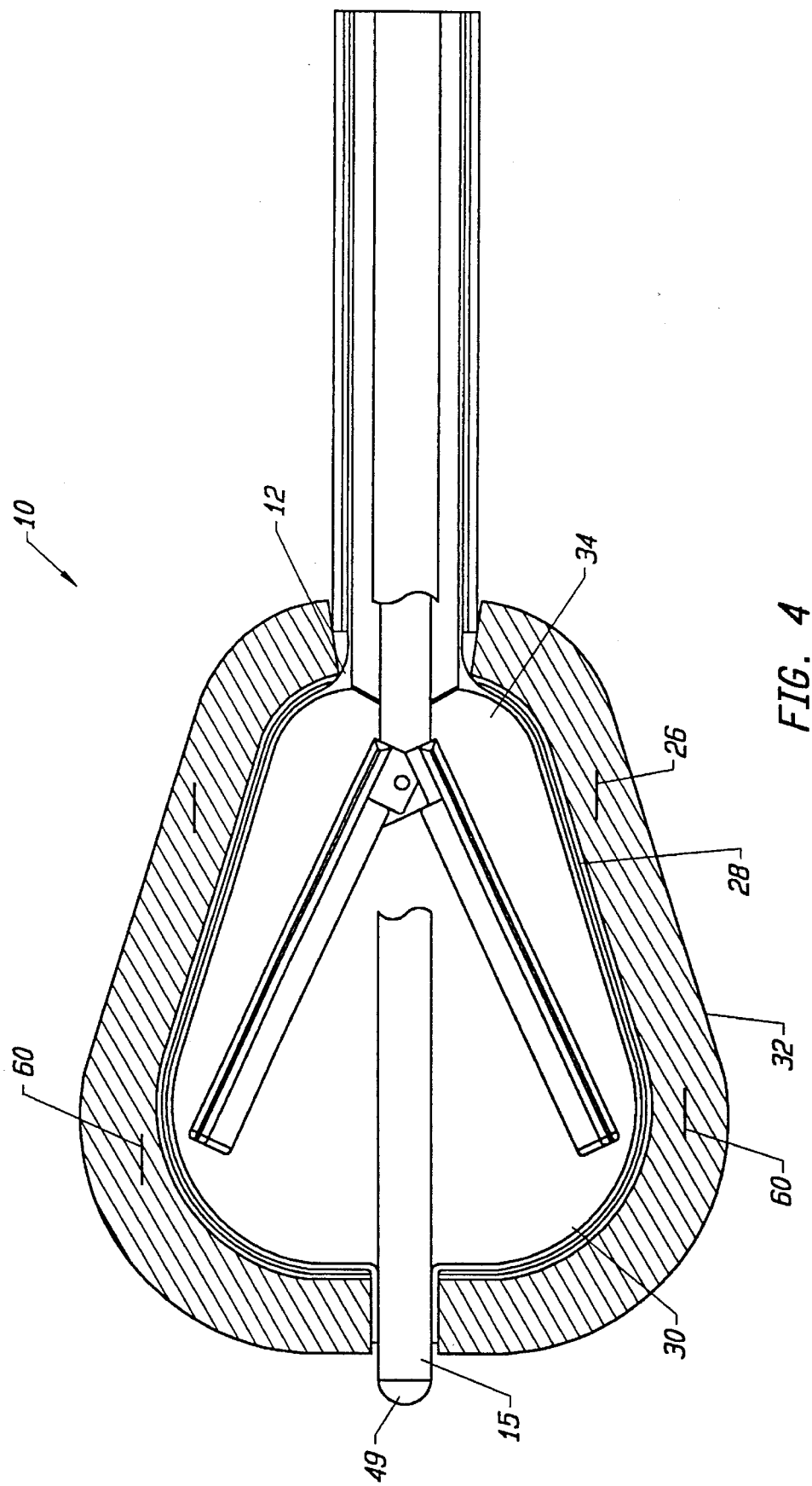
FIG. 4 is a cross-sectional view of the ablation apparatus of the invention with an inflatable device surrounded by a conforming member.

One embodiment of ablation apparatus 10 is illustrated in FIG. 4. In this embodiment, balloon 12 is substantially surrounded by a conforming member 26. Optionally disposed between conforming member 26 and balloon 12 is a membrane 28 that receives electrolytic solution from balloon 12, through a plurality of apertures 30 formed in balloon 12, and passes it to conforming member 26. Alternatively, conforming member 26 can be sufficiently porous to permit the passage of electrolytic solution without the inclusion of formed apertures 30. Membrane 28 can be of the microporous type and made of mylar, expanded PFT such as Gortex available from Gore Company, and the like. Membrane 28 is relatively strong, and sufficiently heat resistant for the amount of thermal energy that is supplied to the endometrium. Membrane 28 applies pressure relative to the electrolytic solution and thus assists in controlling its flow rate.

Figure 5:
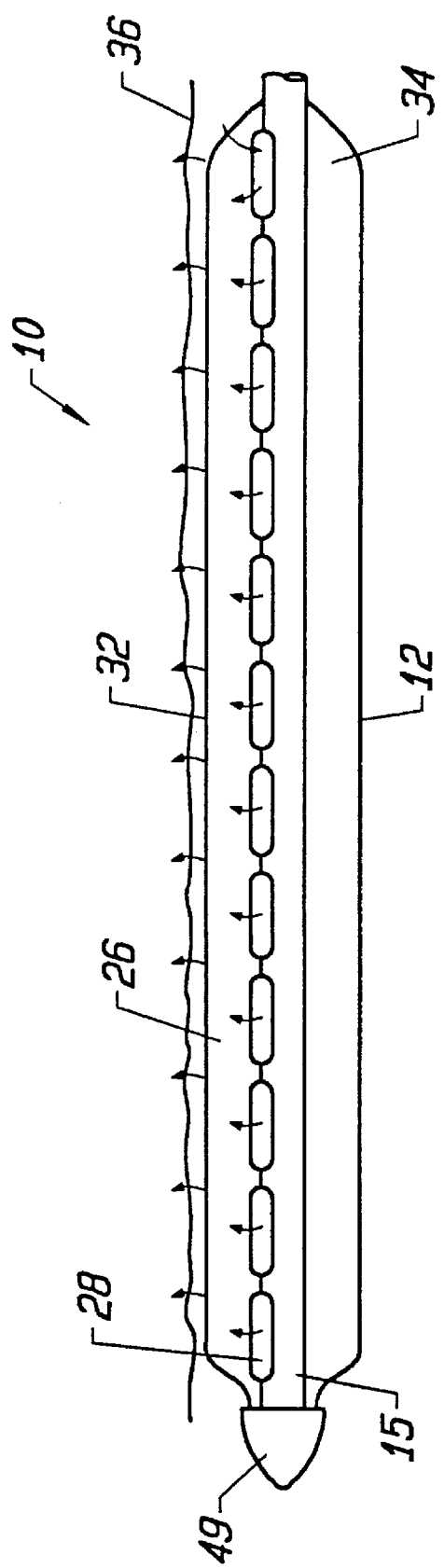
FIG. 5 is a cross-sectional view of the ablation apparatus of the invention with a porous membrane positioned between one side of an inflatable device and a conforming foam structure that is positioned adjacent to an inner layer of an organ.

Membrane 28 can be a heat sealed plenum ( FIG. 5) to distribute electrolytic solution if conforming member is made of a foam type of material. It is not needed if conforming member is a perforated film. In this embodiment, ablation apparatus 10 conforms tightly with the interior of the uterus so that all, or almost all, of the endometrium is in contact with a conductive surface 32 of conforming member 26. In this case, balloon 12 does not have to be moved about the uterus to complete the treatment. Alternatively, ablation apparatus 10 may not entirely fill the uterus and ablation apparatus 10 is then moved about the uterus in order to ablate all of the endometrium, or those sections where ablation is desired.

While a balloon, with a single interior section 34, is the preferred inflatable member, it will be appreciated that the inflatable member can be made of different compositions or materials, with one or more open or closed cells or chambers. The plurality of such cells or chambers can be compressed or configured in a small diameter for insertion and are then expanded after insertion to establish the desired electrical contact with the desired surface of the endometrium.

Interior 34 contains a electrolytic solution, such as saline. The amount of electrolytic fluid in interior 34 is one of the factors for establishing the flow rate of electrolytic solution out of interior 34. Balloon 12 can become more pressurized by increasing the amount of electrolytic solution. As electrolytic fluid enters balloon 12, the pressure within interior 34 increases. This increases the flow rate of electrolytic solution out of apertures 30. A reduction in pressure will correspondingly reduce the flow rate.

Conforming member 26 is made of a material that suitably conforms to a surface 36 that is to be ablated and can have a thickness in the range of about 0.01 to 2.0 cm. Conforming member 26 can be made of a foam type material. Suitable materials include but are not limited to silicon reinforced natural gum rubber, neoprene, soft gum rubber, polyurethane, and the like. Conforming member 26 has characteristics that make it particularly moldable and formable to irregular surfaces. In one embodiment, conforming member 26 is made of a an open cell foam, or alternatively it can be a thermoplastic film such as polyurethane, low density polyethylene, or may be a silicone rubber. Additionally, conforming member 26 can be capable of extruding conductive materials from conforming member 26 itself. Conforming member 26 can be implanted with conductive ions, and conductive surface 32 can be coated with a material that improves its conductivity. The combination of conforming member 26 and the application of the electrolytic solution through conforming member 26 provides for the effective delivery of RF energy to endometrium surface 36.

Figure 6:
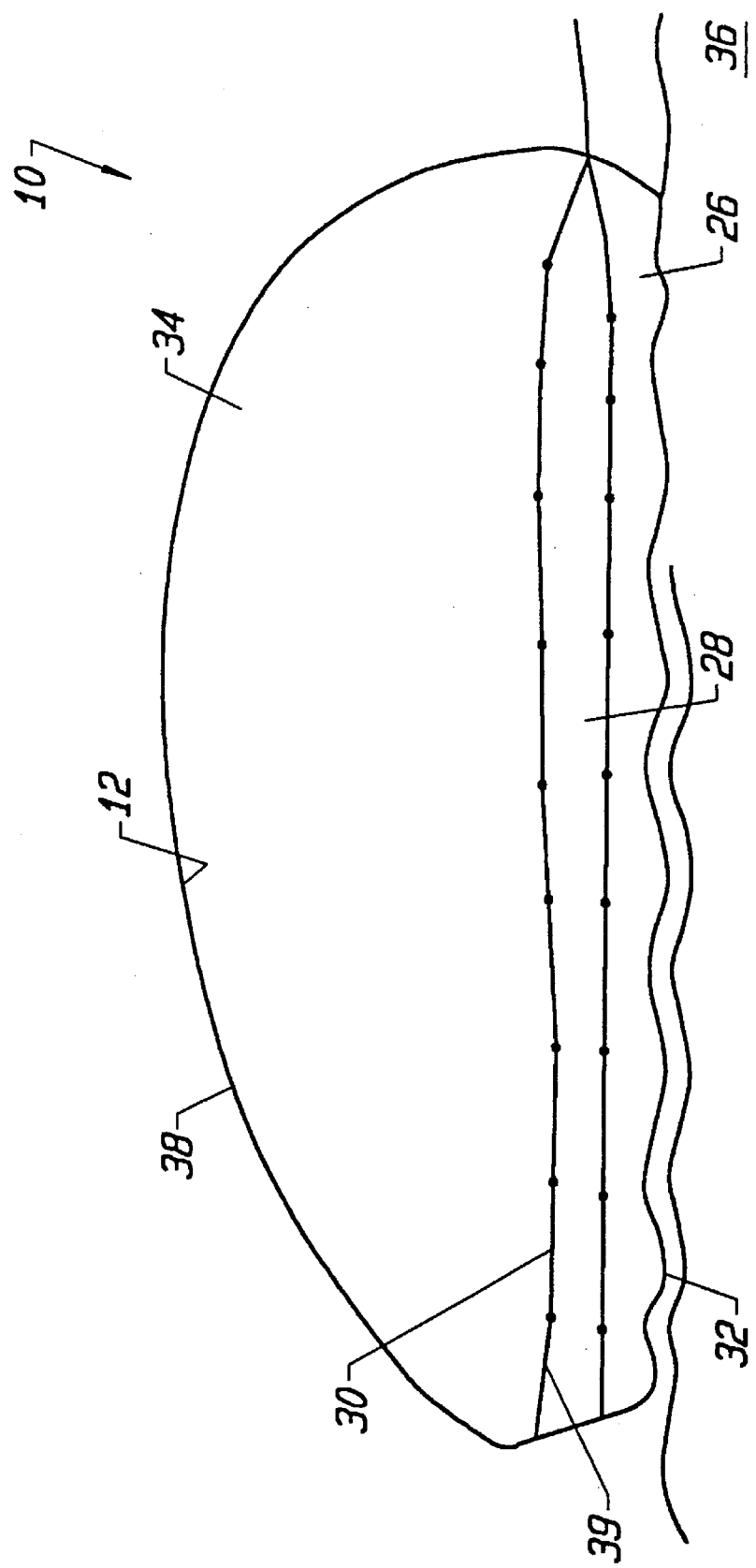
FIG. 6 is a cross-section view of an ablation apparatus of the invention and includes a core lumen that houses illumination and viewing optical fibers, fluid conduits and sensor and electronic cabling.

FIG. 6 illustrates another embodiment of the invention with balloon 12 having a back side 38, and a front side 39 that includes the plurality of apertures 30. In this embodiment, ablative apparatus 10 is moved about the interior of the uterus and back side 38 presses against the interior surface 36 of the uterus.

Figure 7B:
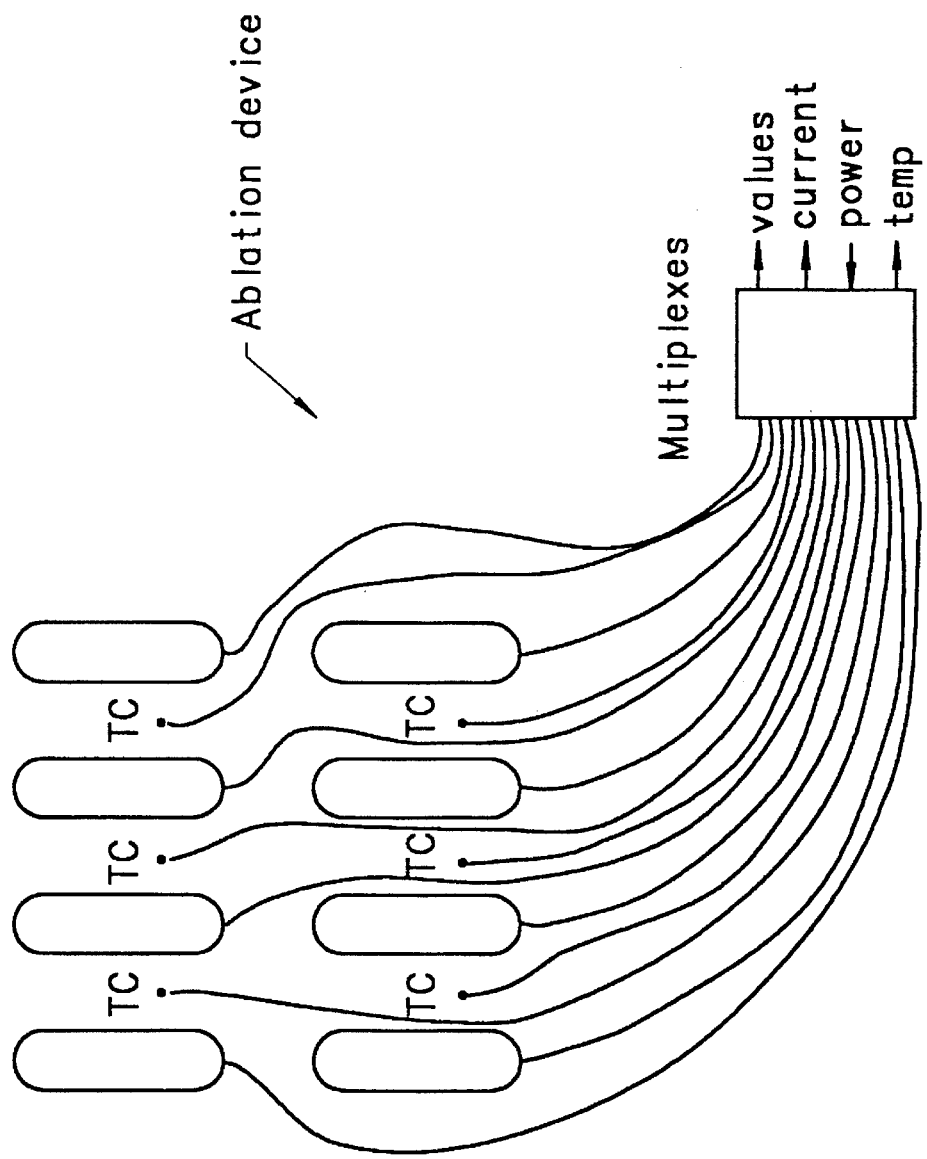
FIG. 7(b) is a second embodiment of the ablation device with individual electrodes positioned on the conforming member in place of the printed circuit of FIG. 7(a).
Figure 8:
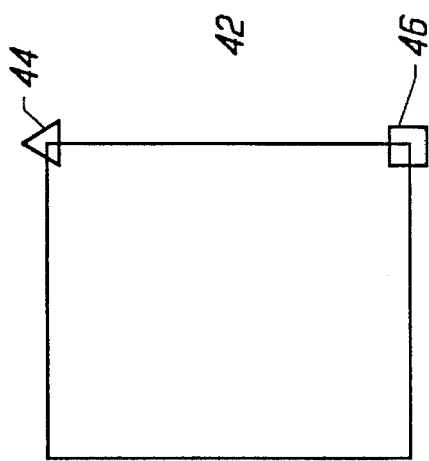
FIG. 8 is a perspective view of one of the segments of the printed circuit shown in FIG. 7(a).

As shown in FIG. 7(a) a printed circuit 40 is deposited, etched or painted with a conductive ink in conforming member 26 or on conductive surface 32. Alternatively, as shown in FIG. 7(b), individual electrodes can be used and multiplexed in either of mono-polar or bi-polar schemes. Printed circuit 40 can be formed by etching, deposition or lithography methods well known to those skilled in the art. Printed circuit 40 can be formed on conductive surface 32, formed on a member that is adjacent to conductive surface, or formed on a member that is adjacent to interior side of conforming member closest to balloon 12. Printed circuit 40 is formed of individual segments 42, as shown in FIG. 8, and is capable of multiplexing so that only certain segments deliver RF energy at a particular time period. Segments 42 cover the entire conductive surface 32 of conforming member 26. Each segment 42 connects to a separate feedwire 43, with all of the wires going to a ribbon connector 45. First, the conductive areas are "printed" and printed circuit 40 formed. Then feedwires 43 are insulated.

In one embodiment of the invention, segments 42 are about 1 cm$^2$ and are approximately 8 mm apart. Segments 42 are volummetrically controlled so that each segment ablates the same volume of the endometrium. Segments 42 are multiplexed, as explained in greater detail in this specification.

RF power can be sequentially supplied to each feedwire 43 in ribbon connector 45, or it can applied to only certain selected feedwires 45, enabling only selected segments 42, along with the electrolytic solution, to deliver RF energy to the endometrium. In this way, printed circuit 40 can be multiplexed. The size of individual segments included with printed circuit 40 is designed to provide the correct current density.

Figure 7D:
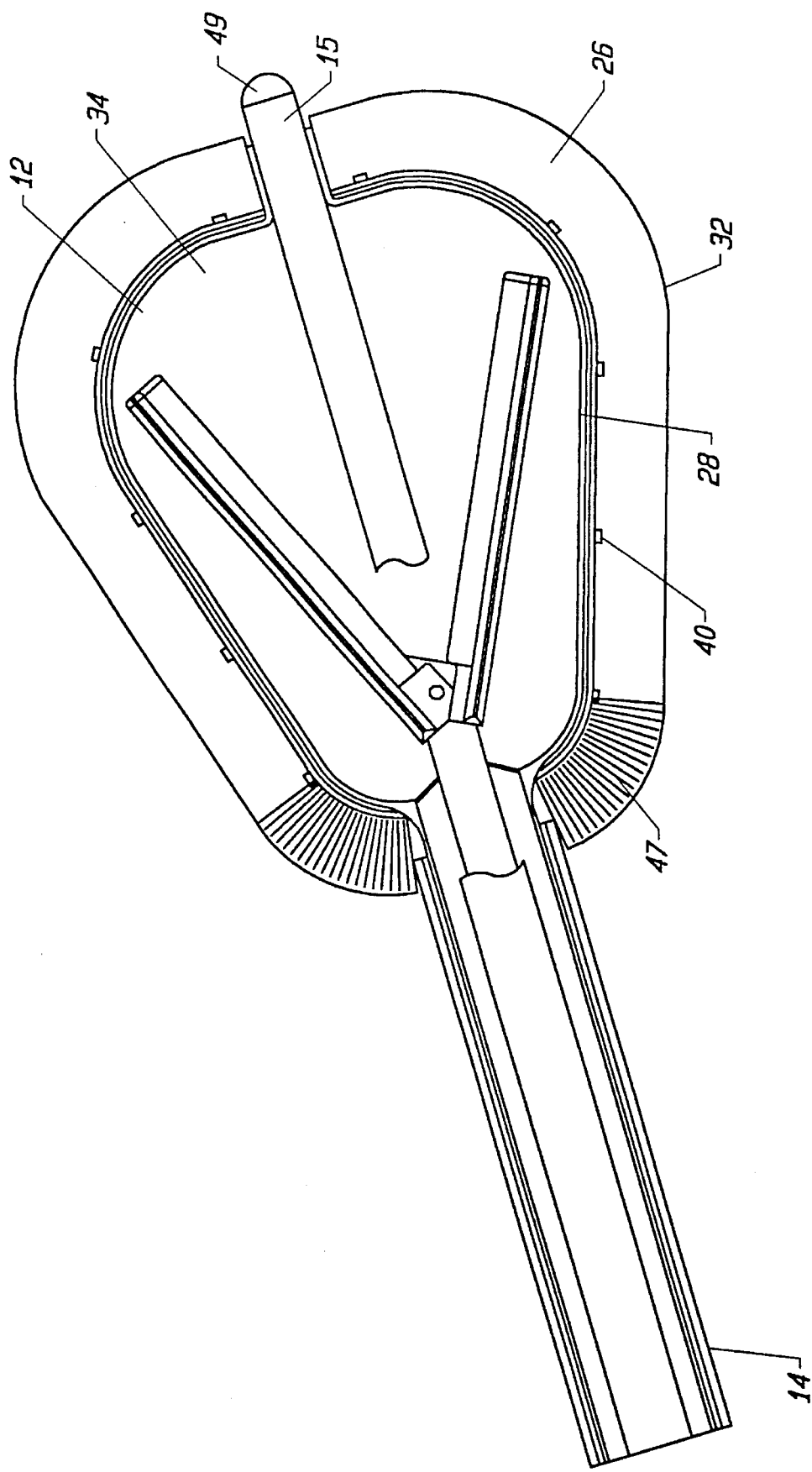
FIG. 7(d) is a cross-sectional view of the ablation apparatus of the invention, with the printed circuit positioned adjacent to an interior side of the conforming member and a plurality of conductive filaments disposed in the conforming member.

In another embodiment of the invention, shown in FIG. 7(c), printed circuit 40 is on a support layer, such as a composite mylar, that is positioned adjacent to an interior surface of conforming member 26. As illustrated in FIG. 7(d) a plurality of filaments 47 can be included in conforming member 26 and serve as a sort of mirror to direct RF energy from segments 42 from an interior side of conforming member 26 to conductive surface 32. Filaments 47 provide the shortest conductive path across conforming member 26. Filaments 47 are made of conductive materials, including but not limited to carbon, silver, stainless steel and the like.

One or more impedance monitors 44 can be used to confirm, before an ablation event, that good coupling of energy is achieved. Also included is one or more temperature monitors/sensors 46 (hereafter "thermal sensors"). Thermal sensors 46 are of conventional design, including but not limited to thermistors, thermocouples, resistive wires, and the like, and are positioned on printed circuit 40. Printed circuit 40 is capable of monitoring circuit continuity in that impedance is monitored between each segment 42 and a ground electrode.

Figure 9:
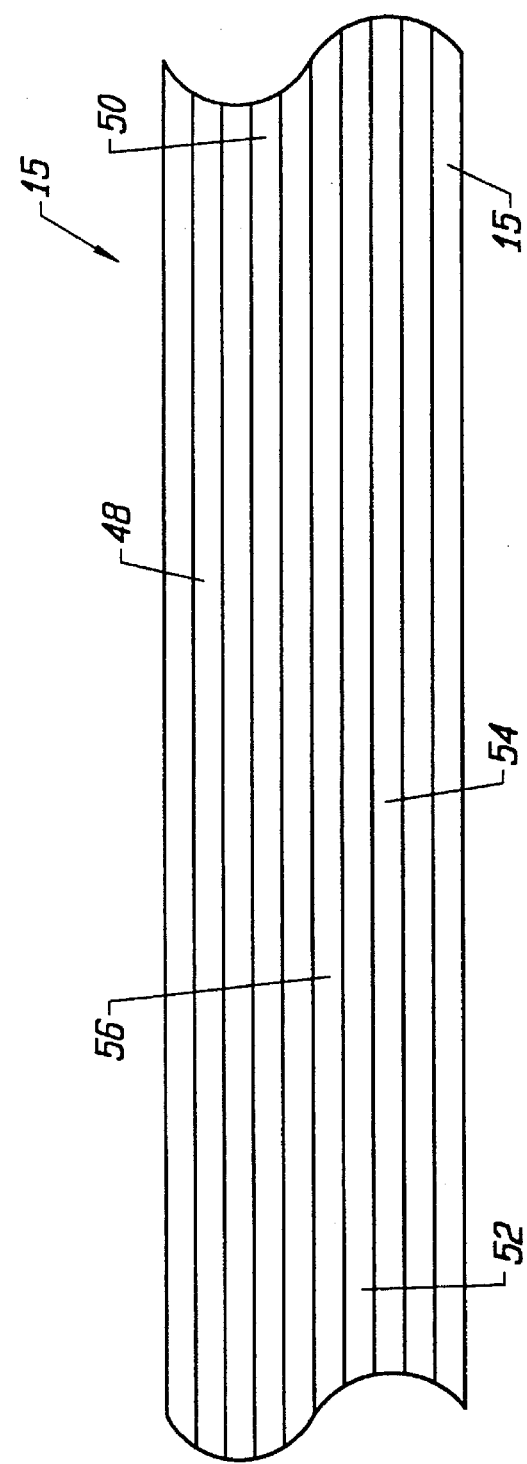
FIG. 9 is a cross-sectional view of the introducer sheath associated with the inflatable device of the invention. Housed in the introducer sheath are viewing and illumination fibers, a tension wire, an RF cable, an ultrasound cable and an electrolytic solution tube.

In FIG. 9, a cross-sectional view of core lumen 15 shows that a variety of conduits, wires and fibers can be housed in the lumen. These include, but are not limited to viewing and illumination optical fibers 48, well known to those skilled in the art, which can deliver light, such as from a Xenon source, to viewing optics 49 (FIG.s 1(a), 1(b) and 1(c); a tension wire 50 that connects to hinge 18; an RF cable 52 connecting feedwires 43 to an RF source; an electrolytic solution delivery conduit 54; and an electrical lead 56 which couples an ultrasound energy source 58 to one or more transducers 60.

Viewing optics 49 can be a 70 degree lens which permits a lateral field of view. Additionally, the combination of optical fibers 48 and viewing optics 49 can be in the form of a flexible viewing scope that is capable of providing a full field of view within the interior of the uterus.

A two-way valve is included with delivery conduit 54. A pump or other similar device advances electrolytic solution to and from balloon 12 through delivery conduit 54. When the procedure is completed, electrolytic solution is removed from balloon 12 through delivery conduit 54. Core lumen 15 is then rotated in a twisting type of motion in order to wrap the entire ablation apparatus 10, e.g., balloon 12, conforming member 26 and membrane 28, around core lumen 15 and substantially all of the electrolytic solution is removed. Ablation apparatus 10 is then retracted back into introducer sleeve 14 and then it is removed from the uterus.

Figure 10:
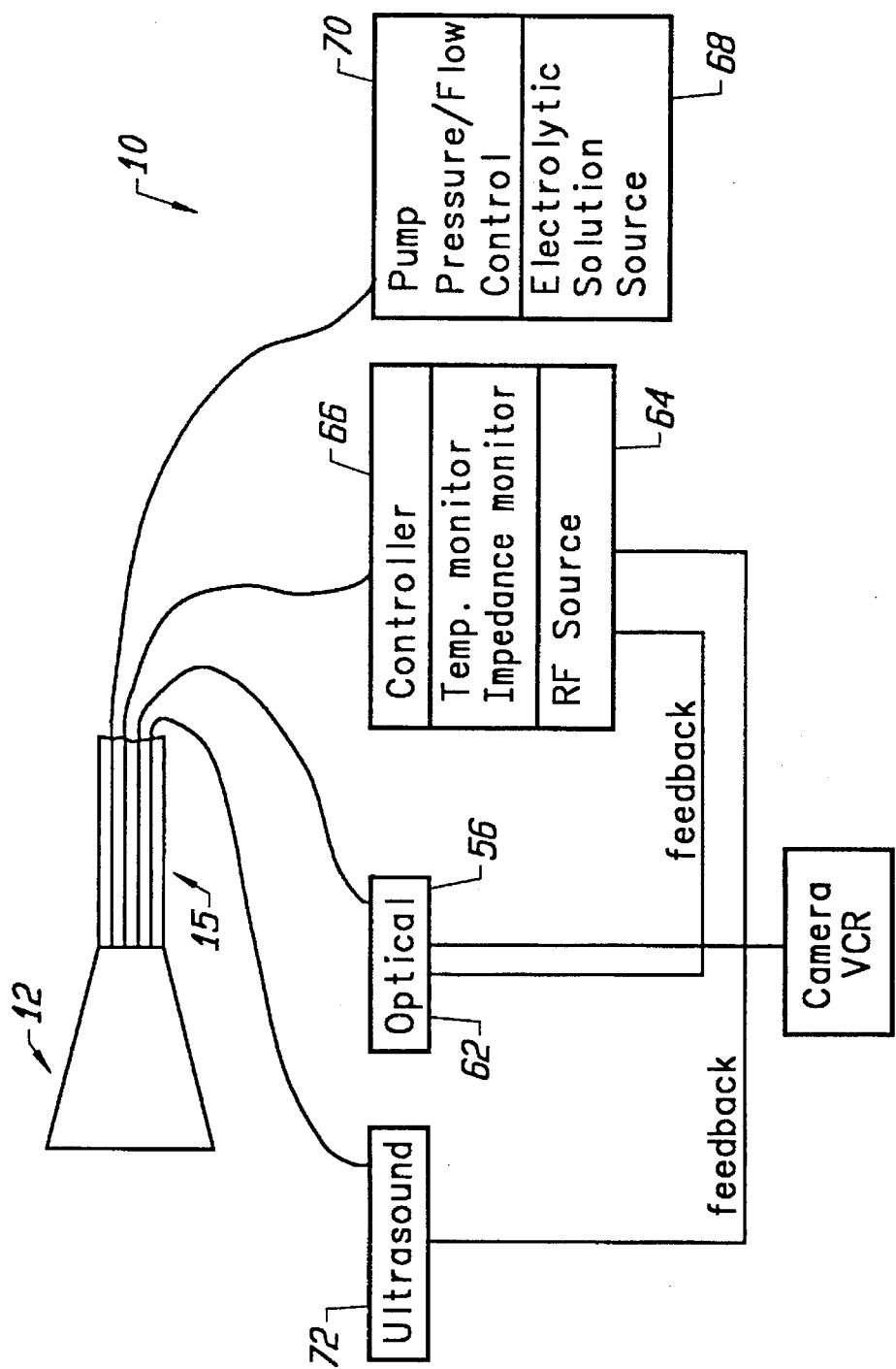
FIG. 10 is a representative block diagram of the invention showing the light, RF, ultrasound and electrolytic sources and their relationships to the inflatable device.

Referring now to FIGS. 2 and 10, a rocker switch 20 operates the rotation and viewing of viewing optics 49, as well as the movement of the flexible scope. A slider switch 21 controls movement of introducer sleeve 14. Slider switch 22 is associated with tension wire 50 and is activated to cause hinge 18 to pivot and impart mechanical movement to balloon 12. Rocker switch 23 is operated by the physician to control the delivery and in certain instances the amount of RF energy from a suitable RF source 64. Rocker switch 24 controls the flow of electrolytic solution to and from balloon 12 to an electrolytic solution source 68. Finally, a switch 25 is associated with ultrasound transducers 60. It will be appreciated that a video camera system can be associated with handle 16.

Further with regard to FIG. 10, an optical system 62 can include a light source, associated illumination and imaging fibers 48 which can be in the form of a flexible endoscope, and associated switch 20 which operates the rotation and viewing of viewing optics 49. Optical system 62 can also include an output going to a VCR, camera, and the like, and a feedback output to RF source 64 and a controller 66. RF source 64 can incorporate a controller, as well as both temperature and impedance monitoring devices. Electrolytic solution source 68 can include a pump/pressure flow control device 70, as is well known to those skilled in the art. An ultrasound source 72 is coupled to one or more ultrasound transducers 60 that are positioned on conductive surface 32. An output is associated with ultrasound source 72 and RF source 64.

Each ultrasound transducer 60 can include a piezoelectric crystal mounted on a backing material. An ultrasound lens, fabricated on an electrically insulating material, is mounted between the piezoelectric crystal and conforming member 26. The piezoelectric crystal is connected by electrical leads 56 to ultrasound power source 72. Each ultrasound transducer 60 transmits ultrasound energy through conforming member 26 into adjacent tissue. Ultrasound transducers 60 can be in the form of an imaging probe such as Model 21362, manufactured and sold by Hewlett Packard Company.

Thermal sensors 46 permit accurate determination of the surface temperature of endometrium surface 36 at conductive surface 32 adjacent to ultrasound transducers 60. Thermal sensors 46 are in thermal proximity to the piezoelectric crystals.

Figure 11:
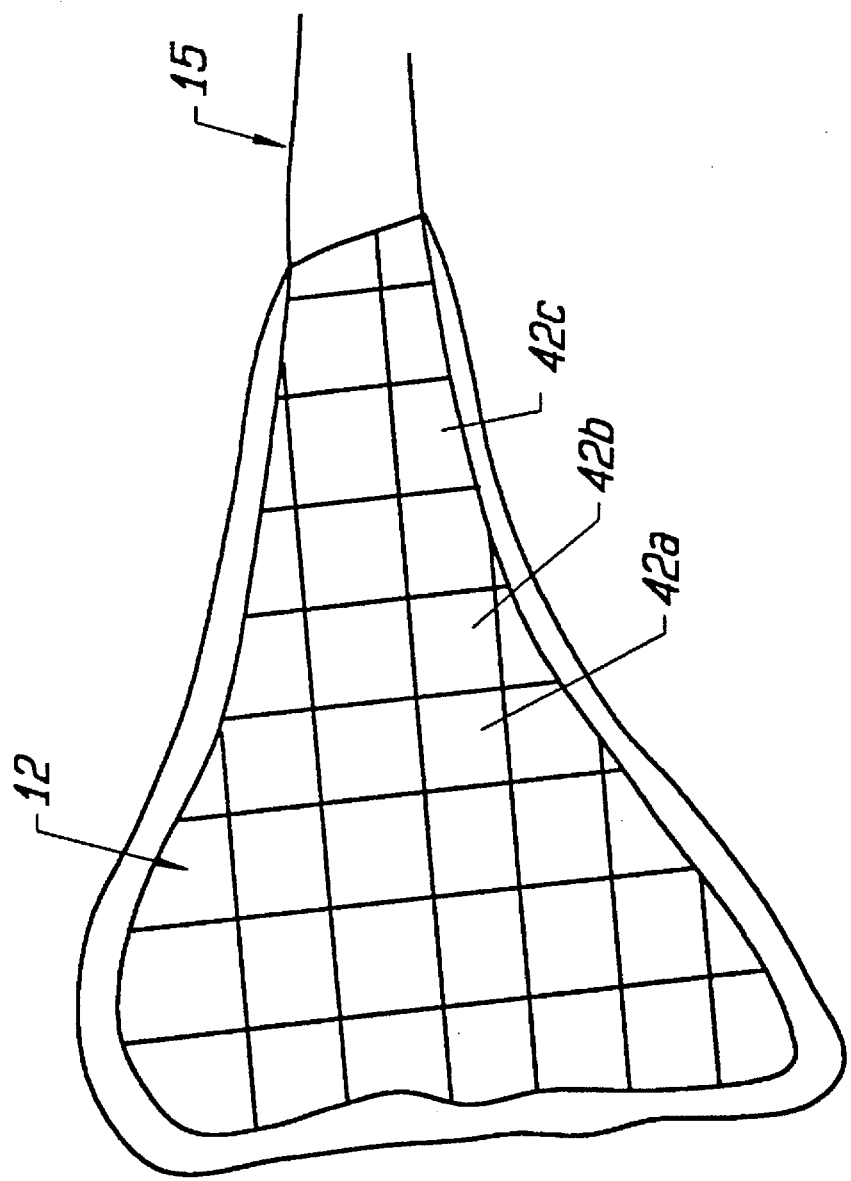
FIG. 11 is a diagram illustrating the positioning of the inflatable device of the invention in the uterus.

As previously mentioned, ablation apparatus 10 can be used with a variety of different body organs. In FIG. 11, ablation apparatus 10 is positioned and retained in the uterus. Individual or a plurality of segments 42 can be activated to ablate the endometrium. Ablation apparatus 10 is multiplexed and delivers RF energy to only certain sections of the endometrium so that, for instance, segment 42(a) is first activated, then segment 42(b), segment 42(c) and so on. For example, each segment can provide 50 watts or less of power and can deliver energy in a bi-polar mode between two adjacent electrodes.

Figure 12:
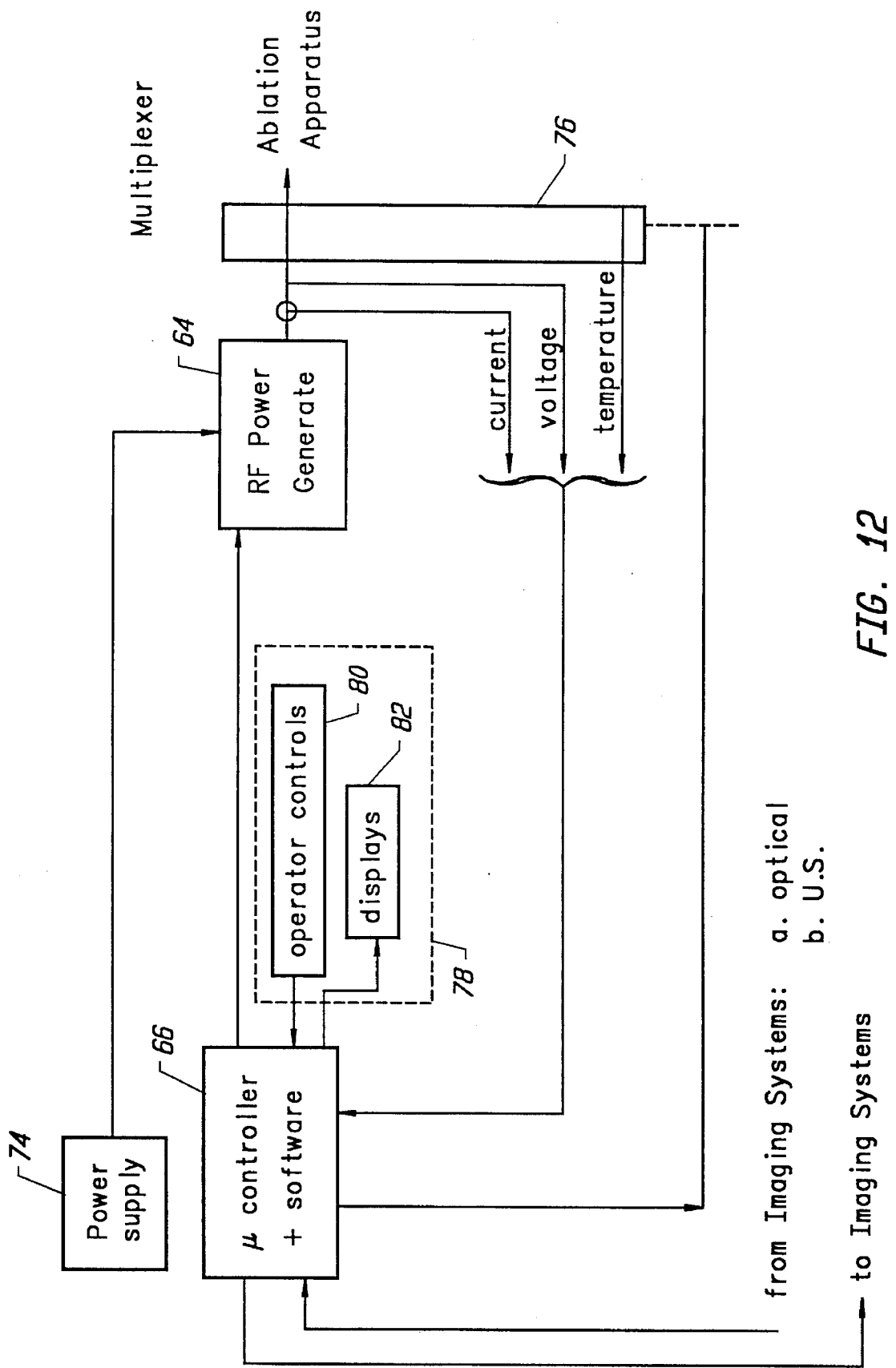
FIG. 12 is a block diagram of an ablation apparatus of the invention that includes a controller and multiplexer.

Referring now to FIG. 12, a power supply 74 feeds energy into RF power generator (source) 64 and then to ablation apparatus 10. A multiplexer 76 measures current, voltage and temperature (at the numerous thermal sensors), going to each segment 42 of ablation device 10. Segments 42 are individually measured during an ablation event at that particular sensor. Multiplexer 76 is driven by controller 66, which can be a digital or analog controller, or a computer with software. When controller 62 is a computer it can include a CPU coupled through a system bus. On this system can be a keyboard, a disk drive, or other non-volatile memory systems, a display, and other peripherals, as known in the art. Also coupled to the bus are a program memory and a data memory.

An operator interface 78 includes operator controls 80 and a display 82. Controller 66 is coupled to the imaging systems, including transducers 60, thermal sensors 46, printed circuit 40 (current and voltage ),.and viewing optics 49 and optical fibers 48.

Current and voltage are used to calculate impedance. Temperature and impedance are measured and then treatment can begin. Preferably, only one segment 42 ablates at a time. Diagnostics are done either optically or through ultrasound. Diagnostics can be performed both before ablation of the endometrium and also after ablation as a check to ascertain the effectiveness of the treatment.

Thermal sensors 46 and sensors contained within RF source 64 measure voltage and current that is delivered to endometrium surface 36. The output for these sensors is used by controller 66 to control the delivery of RF power. Controller 66 also can control temperature and power. An operator set level of power and/or temperature may be determined and this will not be exceeded. Controller 66 maintains the set level under changing conditions. The amount of RF energy delivered controls the amount of power. A profile of power delivered can be incorporated in controller 66, as well as a pre-set amount of energy to be delivered can also be profiled.

Feedback can be the measurement of impedance, temperature and occurs either at controller 66 or at RF source 64 if it incorporates a controller. For impedance measurement, this can be achieved by supplying a small amount of non-therapeutic RF energy. Voltage and current are then measured to confirm electrical contact.

Circuitry, software and feedback to controller 66 result in full process control and are used to change, (i) power (modulate)—including RF, incoherent light, microwave, ultrasound and the like, (ii) the duty cycle (on-off and wattage), (iii) mono-polar or bi-polar energy delivery, (iv) fluid (electrolyte/saline) delivery, flow rate and pressure and (v) determine when ablation is completed through time, temperature and/or impedance. These process variables can be controlled and varied based on tissue temperature monitored at multiple sites on the ablating surface, and impedance to current flow monitored at each segment 42, indicating changes in current carrying capability of the tissue during the ablative process.

Additionally, controller 66 can provide multiplexing, monitor circuit continuity, and/or determine which segment 42 of printed circuit 40 is activated.

Figure 13:
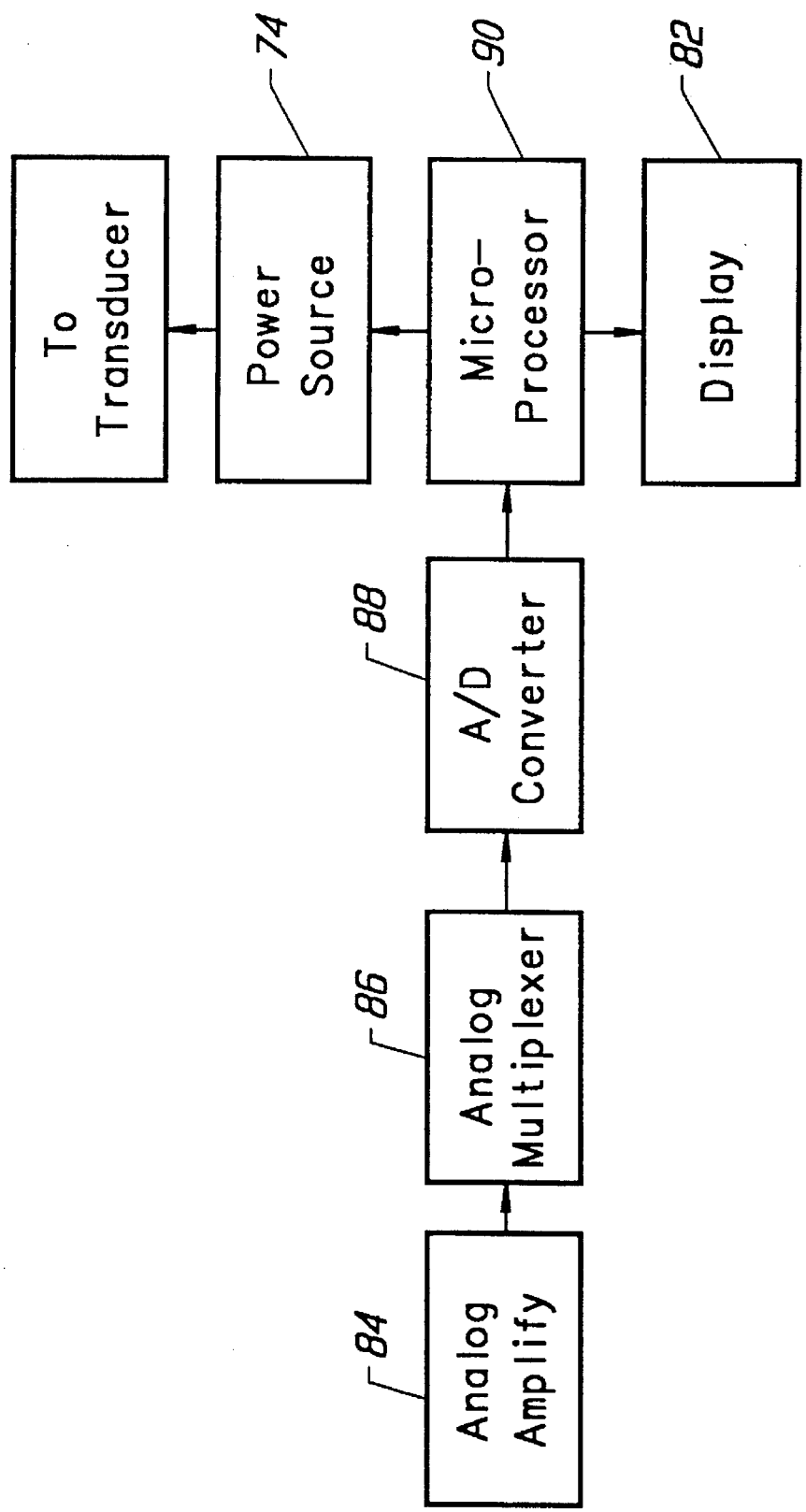
FIG. 13 is a block diagram of one embodiment of a system for processing outputs from the thermal sensors and ultrasound transducers.

A block diagram of one embodiment of suitable processing circuitry is shown in FIG. 13. Thermal sensors 46 and transducers 60 are connected to the input of an analog amplifier 84. Analog amplifier 84 can be a conventional differential amplifier circuit for use with thermistors and transducers. The output of analog amplifier is sequentially connected by an analog multiplexer 86 to the input of an analog to digital converter 88. The output of amplifier 84 is a voltage which represents the respective sensed temperatures. The digitized amplifier output voltages are supplied by analog-to digital converter 88 to a microprocessor 90. Microprocessor 90 calculates the temperature or impedance of the tissue. Microprocessor 90 can be a type 68HCII. However, it will be understood that any suitable microprocessor or general purpose digital or analog computer can be used to calculate impedance or temperature.

Microprocessor 90 sequentially receives and stores digital representations of impedance and temperature at segments 42. Each digital value received by microprocessor 90 corresponds to different temperatures and impedances.

Calculated temperature and impedance values can be indicated on display 82. Alternatively, or in addition to the numerical indication of temperature or impedance, calculated impedance and temperature values can be compared by microprocessor 90 with temperature and impedance limits. When the values exceed predetermined temperature or impedance values, a warning can be given on display 82, and additionally, the delivery of RF energy to that segment 42 is then multiplexed to another segment 42. A control signal from microprocessor 90 can reduce the power level supplied by RF source 64 or can deenergize the power delivered to a particular segment 42.

Thus, controller 66 receives and stores the digital values which represent temperatures and impedances sensed. Calculated surface temperatures and impedances can be forwarded by controller 66 to display 82. If desired, the calculated surface temperature of the endometrium is compared with a temperature limit, and a warning signal can be sent to the display. Similarly, a control signal can be sent to RF power source 64 when temperature or impedance values exceed a predetermined level.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An ablation apparatus for ablating an inner layer in an organ of a body, comprising:

an inflatable member with an exterior surface including a plurality of apertures that communicate with an interior that houses an electrolytic solution, the inflatable member selectively releasing electrolytic solution through the apertures at a flow rate that is dependent on a pressure applied to the inflatable member by the electrolytic solution;

a conforming member with a conductive surface coupled to an RF energy source and a back side in surrounding relationship to the exterior of the inflatable member, the conforming member being made of a material that provides substantial conformity between the conductive surface and a shape of the inner layer of the organ and receives electrolytic solution from the inflatable member and delivers it out of the conductive surface, the conductive surface delivering electrolytic solution and RF energy to the inner layer;

a circuit with segments positioned at one of on the conforming member or in the conforming member for delivering RF energy to selected sections of the inner layer; and a feedback device including an apparatus for detecting a characteristic of the inner layer, the feedback device connected to the RF power source to provide a controlled delivery of RF energy to segments of the circuit in response to the detected characteristic.

2. The ablation apparatus of claim 1, wherein the circuit with segments is formed on a support member positioned adjacent to the conductive surface.

3. The ablation apparatus of claim 1, wherein the circuit with segments is formed on a support member positioned adjacent to the back side of the conforming member.

4. The ablation apparatus of claim 1, wherein the apparatus for detecting the characteristic is a sensor that detects an impedance of the inner layer at a segment.

5. The ablation apparatus of claim 1, wherein the apparatus for detecting the characteristic is a sensor that detects a temperature profile of the inner layer at a segment.

6. The ablation apparatus of claim 1, wherein the inflatable member is a balloon.

7. The ablation apparatus of claim 1, further comprising:

a membrane positioned between the inflatable member and the conforming member and adapted to receive electrolytic solution from the inflatable member and deliver it to the conforming member.

8. The ablation apparatus of claim 1, wherein the conforming member is made of an open and closed cell foam.

9. The ablation apparatus of claim 1, wherein the feedback device includes a controller coupled to the RF power source.

10. The ablation apparatus of claim 9, wherein the feedback device includes a multiplexer coupled to the controller.

11. The ablation apparatus of claim 10, wherein the multiplexer multiplexes segments of the circuit.

12. The ablation apparatus of claim 1, wherein the circuit is a printed circuit.

13. The ablation apparatus of claim 12, wherein the printed circuit includes one or more sensors.

14. The ablation apparatus of claim 1, wherein the feedback device monitors continuity of the circuit.

15. The ablation apparatus of claim 1, wherein the conforming member includes a plurality of conductive filaments.

16. The ablation apparatus of claim 1, wherein the organ is the uterus and the inner layer is the endometrium.

17. The ablation apparatus of claim 1, further comprising:

a deposition of ions in the conforming member to improve conductivity.

18. The ablation apparatus of claim 1, further comprising:

a conductive coating on the conductive surface of the conforming member.

19. The ablation apparatus of claim 1, further comprising:

one or more ultrasound transponders positioned in or on the conforming member.

20. The ablation apparatus of claim 1, wherein the electrolytic solution is a saline solution.

21. An ablation apparatus for ablating an inner layer in an organ of a body comprising:

a first expandable member;

a second expandable member surrounding the first expandable member and attached thereto, the second expandable member having a porous structure to deliver an electrolytic solution to the inner layer of the organ;

a plurality of RF electrodes positioned at one of an exterior of the first expandable member or an interior of the second expandable member;

an electrical connector device connecting the plurality of RF electrodes to an RF energy source;

an electrolytic solution delivery device connected to deliver electrolytic solution to the interior of the second expandable member and wherein the second expandable member expands to conform to at least a portion of the inner layer of the organ; and a feedback device including an apparatus for detecting a characteristic of the inner layer, the feedback device connected to the RF power source to provide a controlled delivery of RF energy to the electrodes in response to the detected characteristic.

22. An apparatus as recited in claim 21 wherein the second expandable member expands in response to the delivery of the electrolytic solution.

* * * * *